United States Patent
Vatter et al.

(10) Patent No.: US 10,071,047 B2
(45) Date of Patent: *Sep. 11, 2018

(54) METHOD TO PROVIDE HAIR SHINE AND COMPOSITIONS TO BE USED THEREIN

(71) Applicant: The Procter & Gamble Company, Cincinnati, OH (US)

(72) Inventors: Michael Lee Vatter, Okeana, OH (US); Kelly Rose Kroger Lyons, Liberty Township, OH (US); Timothy Woodrow Coffindaffer, Maineville, OH (US); Mikah Coffindaffer, Mason, OH (US); Simran Preet Kaur, West Chester, OH (US); Timothy James Felts, Hamilton, OH (US); Scott Edward Smith, Cincinnati, OH (US); Samuel Wolfe Stofel, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/337,142

(22) Filed: Oct. 28, 2016

(65) Prior Publication Data

US 2017/0119655 A1    May 4, 2017

(30) Foreign Application Priority Data

Oct. 28, 2015  (EP) ..................................... 15191944
Oct. 21, 2016  (EP) ..................................... 16195111

(51) Int. Cl.
*A61K 8/89*   (2006.01)
*A61K 8/06*   (2006.01)
*A61K 8/81*   (2006.01)

(52) U.S. Cl.
CPC ................ *A61K 8/89* (2013.01); *A61K 8/062* (2013.01); *A61K 8/8164* (2013.01); *A61K 2800/412* (2013.01); *A61K 2800/42* (2013.01); *A61K 2800/524* (2013.01)

(58) Field of Classification Search
CPC ........ A61K 8/89; A61K 8/062; A61K 8/8164; A61K 2800/412; A61K 2800/42; A61K 2800/524
See application file for complete search history.

(56) References Cited

U.S. PATENT DOCUMENTS

| | | |
|---|---|---|
| 2004/0013698 A1 | 1/2004 | Aust |
| 2008/0069898 A1 | 3/2008 | Smith et al. |
| 2013/0164243 A1 | 6/2013 | Hoffman |

FOREIGN PATENT DOCUMENTS

| | | | |
|---|---|---|---|
| JP | 3948666 B2 | | 8/2004 |
| WO | WO94/08557 A1 | | 4/1994 |
| WO | WO00/06100 A1 | | 2/2000 |
| WO | WO00/06107 A1 | | 2/2000 |
| WO | WO 2000/06107 | * | 2/2000 |
| WO | WO2013037121 A1 | | 3/2013 |

OTHER PUBLICATIONS

Natural Haven Science and Natural Hair 2012.*
Emulsions and Emulsifications 2009, Particle Sciences, Technical Brief 2009, vol. 9.*
U.S. Appl. No. 15/337,098, filed Oct. 28, 2016, Vatter.
"Research Disclosure" Research Disclosure, Mason Publications, Hampshire, GB, vol. 568, No. 19, Aug. 1, 2011, 71 pages.
PCT International Search Report and Written Opinion for PCT/US2016/059247 dated Jan. 24, 2017.
PCT International Search Report and Written Opinion for PCT/US2016/059250 dated Jan. 30, 2017.

* cited by examiner

*Primary Examiner* — Blessing M Fubara
(74) *Attorney, Agent, or Firm* — Alexandra S. Anoff

(57) ABSTRACT

A method is provided which provides shine to hair comprising spraying a leave-on composition to hair with a particle size in the range of from about 0.01 μm to about 10 μm, wherein the resulting film at the dried hair is in the range of from about 100 nm to about 500 nm and more than 25% of the hair fibers are covered. The oil-in water polysiloxane emulsion shows a viscosity of less than 7 Pa*s and a pH value from about 4 to about 8. The emulsion comprises about 0.1% to about 10% by weight of a non-volatile polysiloxane fluid and from about 0.003% to about 0.6% by weight of a rheology modifier, wherein less than 0.015 g of the non-volatile polysiloxane fluid are applied per gram hair.

20 Claims, 3 Drawing Sheets

METHOD TO PROVIDE HAIR SHINE AND COMPOSITIONS TO BE USED THEREIN

TECHNICAL FIELD

This invention relates to a method of providing shine to hair by causing a shift in the chroma band so that the chroma band and the shine band overlap. Further, the chroma band is increased so that the chroma max is greater than the shine max. Providing shine to hair comprises applying hair care leave-on compositions that are applied to the hair after regular washing and conditioning. A thin film in the range of from about 100 nm to about 500 nm of an oil-in-water polysiloxane emulsion having a viscosity of less than 7 Pa*s is applied to the hair, wherein more than 25% of the hair fibers shall be covered by the composition to achieve the effect. Suitable application of the composition to the hair is by spraying with a particle size of the emulsion in the range of from about 0.01 µm to 10 µm. Said method not only provide shine to the hair, but additionally provides a superior shine without the traditional drawback of greasiness. Thus, the method helps clean hair to stay clean, but not greasy. The composition applied by the method described herein can stay onto the hair providing an additional protection against environmental influences, such as dust, ozone or sun shine and additionally provide thermal protection, frizz control, conditioning and detangling.

BACKGROUND OF THE INVENTION

The shampooing of hair conventionally is performed utilizing any of numerous detersive surfactant-containing compositions known in the art. However, the combination of frequent shampooing, environmental factors, and the natural condition of one's hair can result in the hair not having a healthy, lustrous appearance. In particular heavily damaged hair looks matted and dull. One of the most effective ways of addressing this problem is through the use of hair conditioning compositions that improve the shine of the hair. A highly effective technology for this purpose is the use of a combination of a high refractive index polysiloxane fluid, such as phenylated polysiloxane, with a spreading agent, such as a polysiloxane resin as disclosed in WO 94/08557 (Brock et al., Procter & Gamble, published Apr. 28, 1994).

It is also highly desirable to provide hair treatment compositions, especially leave-on compositions that can improve the appearance of hair without the heaviness of other conditioners, which can make hair feel unwashed. This can be important for hair care products containing the above combination of phenylated silicone and spreading agent since they can impart to the hair a coated feeling that is not especially desirable on the part of the consumer. This problem is exacerbated by leave-on products. Although leave-on products are highly desirable from the standpoint of providing excellent shine to the hair versus rinse-off products, they can result in excess phenylated silicone/spreading agent being left on the hair, and this can have detrimental effects upon clean hair feel and look, such as silicone bridges between individual hairs imparting a wet or greasy feeling and look to the consumer such as achieved with the products of JP3948666 B2.

Sensates such as menthol and camphor can be used in leave-on products to provide a sense of refreshment, however these do not totally overcome the issue of overall hair heaviness, which must include a solution the hair feeling coated by the phenylated silicone/spreading agent combination. WO00/06100A1 and WO00/06107 (both Young et al., Procter & Gamble, published Feb. 10, 2000) suggest solving this problem by using ethanol containing compositions under certain conditions. Ethanol however must be used at relatively high levels in order to achieve maximum levels of refreshment and clean hair feel. Unfortunately when used at these levels, ethanol can cause the scalp to become dried out, leading to the skin feeling itchy or to suffer from flaking. In addition, ethanol may cause drying of the hair.

The present invention deals with the problem of hair shine more generally. It is an object of this invention to provide a method that can provide excellent shine without drying out the hair or scalp and without imparting wet or greasy look and heavy feeling to the hair. The parameters needed therefor should be determined and formulated into a hair care composition, especially a leave-on composition, which shall be applied to the hair.

SUMMARY OF THE INVENTION

The above object can be achieved by a method of applying a combination of a shine agent with a viscosity of less than 7 Pa*s comprising a polysiloxane in conjunction with a small level of a shining surfactant to the hair, wherein the shine agent has to be applied in a specific film thickness and the emulsion is applied by spraying with a specific particle size.

It is an object of the present invention to provide a method of providing shine to hair comprising applying a leave-on composition comprising an oil-in water (silicone-in-water) emulsion having a viscosity of less than 7 Pa*s and a pH value in the range of from about 4 to about 8 to the hair, wherein the emulsion comprises about 0.1% to about 10% by weight of a non-volatile polysiloxane fluid and wherein less than 0.015 g of the non-volatile polysiloxane fluid are applied per g of hair,
wherein the emulsion is applied by spraying with a particle size of the emulsion in the range of from about 0.01 µm to about 10 µm,
so that the film thickness of the non-volatile polysiloxane fluid at the hair after drying is in the range of from about 100 nm to about 500 nm,
wherein the composition is applied to more than 25% of the exposed hair fibers.

The composition may further comprise from about 0.003% to about 0.6% by weight of the emulsion of a rheology modifier in order to increase composition stability over time.

The method uses polysiloxane silicone-in-water emulsions as leave-on compositions, which are sprayed to wet and/or dry hair and are allowed to dry on hair without first being rinsed off. The composition can be delivered best by spraying to the wet and/or dry hair, preferably in an amount of less than 1.2 mg of the non-volatile polysiloxane fluid per $cm^2$ hair.

In a preferred embodiment the method applies a composition comprising:
(a) from about 0.1% to about 10.0% by weight of the composition of a non-volatile polysiloxane fluid;
(b) from about 0.02% to about 5.0% by weight of the composition of a shining surfactant;
(c) from about 0% to about 0.6% by weight of the composition of a rheology modifier comprising an acrylic acid/Vinyl ester copolymer; and
(d) a carrier suitable for the application to the hair, wherein the composition is optionally free of ethanol.

In a further preferred embodiment the method applies a composition comprising:

(a) about 4.5% to about 5.5% by weight of the composition of polydimethylsiloxane;
(b) about 0.1% to about 0.8% by weight of the composition of polydimethylsiloxane copolyol;
(c) from about 0.05% to about 0.3% by weight of the composition of acrylic acid/Vinyl ester copolymer as rheology modifier;
(d) a carrier suitable for the application to the hair comprising perfumes, preservatives, citric acid and water; and
(e) optionally from about 0.1 to about 1.0% by weight of the composition of an anionic surfactant,
wherein the viscosity of the emulsion is less than 2 Pa*s, preferably in the range from about 0.5 to about 0.7 Pa*s.

In another preferred embodiment the method applies a composition comprising:
(a) about 0.1% to about 10.0% by weight of the composition of polydimethylsiloxane;
(b) about 0.05% to about 1.0% by weight of the composition of polydimethylsiloxane copolyol;
(c) from about 0.05% to about 0.6% by weight of the composition of acrylates/vinyl isodecanoate crosspolymer as rheology modifier;
(d) preferably from about 0.1 to about 1.0% by weight of the composition of an anionic surfactant as secondary surfactant; and
(e) a carrier suitable for the application to the hair comprising perfumes, preservatives, citric acid and water,
wherein the viscosity of the emulsion is less than 7 Pa*s and the ratio of the non-volatile polysiloxane fluid to polydimethyl polydimethylsiloxanes copolyol is in the range of about 90% polydimethylsiloxane to about 10% polydimethylsiloxane.

It is a benefit of the present invention that the method can provide a non-heavy and non-greasy feeling to the hair in combination with excellent and brilliant hair shine. The method can also be characterized as providing low levels of tackiness and greasiness while providing excellent shine. The present method can also provide conditioning to the hair through the use of the shine agent as well as through the use of additional ingredients as well be described below.

DETAILED DESCRIPTION OF THE INVENTION

Figure 1A:
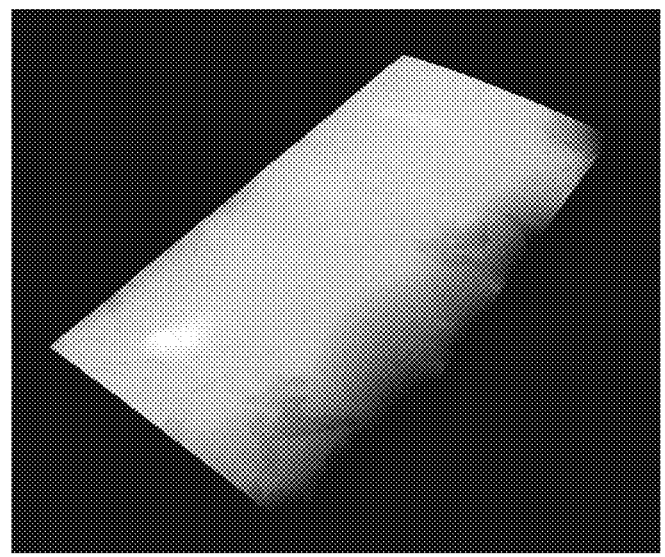
FIG. 1A shows a 3D laser image of a hair fiber after being treated with about 1.6 g of the composition of Example M.

The essential components, aspects and method steps of the invention, as well as various optional and preferred ingredients and embodiments of the invention are described in further detail below.

All percentages and ratios used hereinafter are by weight of the total composition unless otherwise indicated. Unless otherwise indicated, all percentages, ratios, and levels of ingredients referred to herein are based on the actual amount of the ingredient, and do not include solvents, fillers, or other materials with which the ingredient may be combined as commercially available products.

Active and other ingredients useful herein may be categorized or described herein by their cosmetic benefit or their postulated mode of action or function. However, it is to be understood that the active and other ingredients useful herein can, in some instances, provide more than one cosmetic benefit or function or operate via more than one mode of action. Therefore, classifications herein are made for the sake of convenience and are not intended to limit an ingredient to the particularly stated function(s) or activities listed.

As used herein, the word "comprise," and its variants, are intended to be non-limiting, such that recitation of items in a list is not to the exclusion of other like items that may also be useful in the materials, compositions, devices, and methods of this invention. This term encompasses the terms "consisting of" and "consisting essentially of".

As used herein, the word "include," and its variants, are intended to be non-limiting, such that recitation of items in a list is not to the exclusion of other like items that may also be useful in the materials, compositions, devices, and methods of this invention.

The invention hereof can comprise, consist of, or consists essentially of the essential elements described herein as well as any of the preferred or other optional ingredients described herein.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

All measurements referred to herein are made at 22° C. (i.e. room temperature) unless otherwise specified.

As used herein, the word "about" means+/−10 percent.

METHOD OF USE

According to the method of the present invention a leave-on composition is applied to the hair. Said composition can be applied to the hair and scalp in conventional ways to provide shine, conditioning, and the clean feel and refreshment benefits of the present invention. Such method depends upon the type of composition employed but generally involves application of an effective amount of the leave-on composition to the hair or scalp. The composition is a leave-on product which is sprayed onto the hair and the composition is then allowed to remain on the hair to dry, without rinsing. Thus, the hair spray which may contain adhesive hair setting polymers, is sprayed onto hair which has already been manipulated to the desired style.

Hairs to which a leave-on composition was applied by the method as disclosed herein appear shiny and healthy. Shine is based on the interactions of light with hair fibers. The main interactions are reflection by the surface of the fiber, which creates a shine band, travelling through the fiber and reflection thereafter which creates a chroma band or the light may be also scattered inside the hair fiber which creates diffused light. Usually more light is reflected directly so that the shine band is larger than the chroma band. Without being bound to a theory, it is believed that the described apparent shine can be achieved by causing a shift in the chroma band so that the chroma band and the shine band overlap. Further, the chroma band is increased so that the chroma max is greater than the shine max. Surprisingly, it was found that after treating hair with the method of the present invention more light travels through the fiber thereby producing a larger chroma band compared to the shine band. Due to the larger chroma band a more brilliant shine effect could be achieved. Optimal results are achieved with hair already having a chroma band, i.e. hair that is not black.

Rating systems are also known in the art in order the make shine reproducible. A suitable system to calculate consumer relevant shine in a reproducible manner is the Reich-Robbins luster value. Hair which was treated according to the method of the present invention shows a Reich-Robbins luster value ($L_{Reich-Robbins}$) of greater than 44. Control hair which was not treated by the method as disclosed herein shows a Reich-Robbins luster value ($L_{Reich-Robbins}$) of 30. Thus, an increase of >35% was achieved by the method of the present invention.

In order to achieve said shift in chroma band the roughness of the hair is equalized by applying a specific leave-on composition in an amount to form a film with a thickness of a non-volatile polysiloxane fluid at the hair in the range of from 100 nm to 500 nm after drying.

Therefore, a composition is applied comprises a polysiloxane emulsion having a viscosity of less than 7 Pa*s, wherein the emulsion comprises about 0.1% to about 10% by weight of a non-volatile polysiloxane fluid. It is important to achieve the intended effect that less than 0.015 g of the non-volatile polysiloxane fluid are applied per gram of hair, but that more than 25% of the hair fibers are covered by the composition. A further important aspect of the present invention regarding the application of the composition is the particle size of the emulsion droplets which are sprayed. The particle size of the droplets according to the present invention are in the range of from about 0.01 μm to about 10 μm, preferably in the range of from about 0.1 μm to about 1 μm, more preferred in the range of from about 0.3 μm to about 0.8 μm. The particle size defined herein helps to spread the composition over the hair without the formation of silicone bridges between adjacent hair fibers and helps to spread the composition over the hair homogeneously, as irregular film thickness as well as the formation of silicone bridges impart to greasy appearance of the hair.

Preferably the polysiloxane emulsions are silicone in water (si/w) emulsions. However also in scope with the invention are oil-in-silicone-in-water (o/si/w) emulsions, or water-in-silicone-in oil-in-water (w/si/o/w) emulsions. The commonality in the emulsions of this invention is that the continuous phase is water, whereas the discontinuous phase may be silicone or oil.

The compositions can be applied to either wet or dry hair. As used herein, wet hair also includes damp hair. Generally less than 1.2 $mg/cm^2$, preferably less than 1.005 $mg/cm^2$, more preferred less than 0.8 $mg/cm^2$, most preferred less than 0.2 $mg/cm^2$ of the non-volatile polysiloxane fluid is applied to the hair and scalp, however these amounts can vary by preference of the user or for selected applications, such as those limited to specific portions of the hair and scalp. The resulting dose of the composition, in particular of the non-volatile polysiloxane fluid is less than 0.015 g, preferably less than 0.012 g, more preferred less than 0.01 g per gram of hair. Said amounts given herein are still sufficient to provide the hair shine benefit, also named the "effective amount" in the following.

The effective amount is usually applied with several pumps of spray as it is not possible to cover the whole surface of the hair with one pump. A suitable amount which might be applied in one pump according to the present invention is about 0.2 g leave-on composition per pump. A suitable distance between the nozzle and the hair is in the range of from about 10 cm to about 15 cm. It is intended that more than 25% of the area the emulsion was applied to, preferably more than 30% of the area the emulsion was applied to, more preferred more than 40% of the area the emulsion was applied to comprise droplets of the emulsion in order to achieve a homogeneous shine after drying. The contact angle on the wet hair is less than 95°, preferably less than 90°, more preferred less than 85°. Contact angles are measured as disclosed below.

The composition applied to the hair forms a film which covers the hair. For a sufficient and homogeneous shine effect after drying more than 25% of the hair fibers, preferably more than 35% of the hair fibers, preferably more than 50% of the hair fibers should be covered with the composition, wherein even with higher number of coverage substantially no bridging of hair fibers was observed. The disclosed effect is achieved with even small amounts of coverage as the composition is applied to the outmost exposed hair fibers on the external surface that can be seen. To achieve a good shine impression it is important that the shift in chroma band is achieved with the top layer of the hair while the hairs which are located underneath the top layer, still might participate in light reflection.

For the effects to be achieved with the method as disclosed herein it is also important that although the top layer is covered, substantially no silicone bridges are built between the individual hair fibers. Formation of silicone bridges is one important factor for an unpleasant feeling and a greasy appearance. "Substantially no silicone bridge formation" as used herein shall mean that less than 25% of hair fibers, preferably less than 15% of hair fibers, more preferred less than 5% of hair fibers, more preferred less than 1% of hair fibers, more preferred less than 0.1% of hair fibers are bridged by the non-volatile polysiloxane fluid with its adjacent fiber. That means by the method of the present invention a film around each individual hair is substantially formed. In particular, a thin film is formed by the leave-on composition with a film thickness of the non-volatile polysiloxane fluid at the hair after drying in the range of from 100 nm to 500 nm, preferably in the range of from 100 nm to 400 nm, more preferred in the range of from 100 nm to 300 nm. The thicker the film the greater is the risk of formation of silicone bridges and the appearance of greasiness.

Thus, the combination of the method of application, including but not limited to, spraying, droplet size, amount applied per g hair and per $cm^2$ hair, film thickness onto the individual hair fiber and the properties of the composition, including but not limited to, viscosity and compounds such as the non-volatile polysiloxane fluid form the shine appearance of the hair without the greasy appearance.

As already discussed above the perfect shine can be imparted to the hair by applying a leave-on composition as disclosed herein. Specific working combinations and example compositions are shown in the following, but the invention is not limited to the ranges and combinations mentioned explicitly. Other ranges might be suitable as well as long as they do not contradict gist and scope of the present invention, in particular as long as they do not negatively affect the shine of the hair.

The essential and optional components of the compositions used for the method as disclosed herein are described in the following paragraphs:

Hair Care Product

The compositions used in the methods of the present invention are advantageous for utilization in connection with a wide variety of hair care products, comprising a hair care composition which is suitable for application to the hair and imparts shine to the hair. The hair care products disclosed herein are especially sprays.

The compositions used in the method of the present invention provide shine to hair by droplets which are spread over the hair and form a film of the composition. The compositions are polysiloxane emulsions comprising a viscosity of less than 7 Pa*s. Preferably the composition is less viscous, in particular the viscosity is less than 5 Pa*s, more preferred less than 2 Pa*s, more preferred less than 1 Pa*s and most preferred in the range from 0.5 to 0.7 Pa*s. The viscosity of the composition is important regarding the application and the spreading of the composition.

Preferably the polysiloxane emulsions are silicone in water (si/w) emulsions. However also in scope with the invention are oil-in-silicone-in-water (o/si/w) emulsions, or water-in-silicone-in oil-in-water (w/si/o/w) emulsions. The commonality in the emulsions of this invention is that the continuous phase is water, whereas the discontinuous phase is silicone or oil.

In addition or alternatively, the pH value of the composition is adjusted automatically by the compounds formulated or it might be adjusted to a special value by adding an acidic solution, such as citric acid. A suitable pH value for the composition used in the method of the present invention is in the range of from about 4 to about 8, preferably in the range of from about 5 to about 7.

The hair care products hereof can also comprise a package for containing the composition. A wide variety of suitable packages are known in the art. They will generally be characterized by dispensing orifices through which the product can be poured, shaken, pumped, squeezed, or sprayed.

The products used in the methods as described herein are leave-on products. By leave-on composition is meant that the composition is applied to the wet and/or dry hair and allowed to remain on the hair to dry without first being rinsed off. The leave-on composition can be of any type suitable and intended to be applied to the hair and used in a leave-on manner. Without limitation, these include the above mentioned tonics, gels, creams, pastes, and sprays (aerosols, non-aerosols) including hair sprays which condition and/or style the hair.

The leave-on compositions used herein will be free of cleansing-effective levels of cleansing surfactants, such as anionic or amphoteric surfactants, which are generally present in compositions such as shampoos. In general leave-on compositions will contain no more than 5% by weight of such surfactants, preferably no more than 3% by weight of such surfactants, more preferred no more than 2% by weight of such surfactants, more preferred no more than 1% by weight of such surfactants most preferred no more than 0.5% by weight of such surfactants and can be as low as about zero percent.

The leave-on compositions as used herein can also include with their packaging instructions in the manner of use consistent with the method as disclosed herein.

By "spray" what is meant herein is a product that upon use dispenses the composition in the form of droplets dispersed in the ambient air (liquid-in-gas dispersion). The spray products hereof will comprise compositions which are characterized by having at least about 50%, preferably at least about 70%, more preferred at least about 80% by volume of the spray droplets having the leave-on composition with an emulsion particle size in the range of about 10 μm to about 10 nm, in particular in the range of from about 1 μm to about 100 nm, more particular in the range of from about 800 nm to about 300 nm or any other numerical range which is narrower and which falls within such broader numerical range, as if such narrower numerical ranges were all expressly written herein. The percentage by volume as used herein refers to the percentage of fluid sprayed having particles sizes within the referenced ranges based on the total fluid volume sprayed. The particle size as given herein refers to the diameter of the emulsion droplets in the composition.

Spray droplet emulsion particle size is determined by laser diffraction (such as with a Malvern 30 Instruments 2600C particle size analyzer or equivalent) using the International Organization for Standardization (ISO) Standard Method ISO/WD 13320. Without intending to be limited by theory, it is believed that smaller spray particles provide a more uniform/even distribution/deposition across the hair fiber surface preventing high concentrations of the leave-on composition in a small area and thereby preventing a greasy appearance due to irregular covering as well as preventing the non-volatile polysiloxane fluid from bridging between individual hair fibers. Consequently, the particle size represents one important factor in order to provide the desired level of performance without imparting greasiness to the hair. It is to be understood that the spray products do not include mousses, which although they can be dispensed via aerosol or non-aerosol packages, they do not actually provide a dispersion of droplets in ambient air in the same manner as a conventional spray. The compositions can be solutions, liquid-in-liquid dispersions, emulsions, microemulsions, liquid crystalline, or any other form except as indicated below, suitable for application to the hair and scalp.

An optimal spray pattern could be achieved by spraying of the compositions as disclosed herein. A spray efficiency of greater than 50%, preferably greater than 60% could be achieved, wherein spray efficiency is calculated according to the following formula:

$$\text{Efficiency} = (\text{Dose (g/stroke)}/\text{Area (inches)} * \% \text{ fill} * D50(\text{particle size}) * \text{Dep \%}) * 100$$

"DEP" as used herein stands for deposition [%] and is calculated as" the actual amount sprayed/amount deposited on the substrate*100; i.e. the weight (g) of the filter paper after spraying–weight (g) of the filter paper before spraying/ amount sprayed (g)*100.

The deposition percentage (DEP %) was determined by spraying the product at a 90 degree angle, at a predetermined distance, onto a sheet of filter paper and weighing the filter paper before and after spraying. Spray pattern was analyzed with a nozzle-to-paper distance of 4 inches, 5 inches or 6 inches, with a typical spray duration of 2 seconds for aerosol and 1 to 2 pumps for non aerosol. A suitable filter paper for this method is Whatman filter paper, 150 mm Several areas were analyzed and the % fill was determined by visual assessment of how much of the spray area contained the composition. The best dose for spray analysis was 0.2 g/stroke. The average droplet size (D50) of the preferred atomized spray was about 70 μm to 75 μm. An efficiency of greater than 50% could be achieved for example with an Aptar spray nozzle and Aptar Euro Mist 0.19 mL Pump.

Hair Shine Agent

The leave-on compositions used in the method of the present invention comprise polysiloxane emulsions comprising 0.1% to 10% by weight of a non-volatile polysiloxane fluid. Preferably, the non-volatile polysiloxane fluid is mixed together with a shining surfactant, preferably a polydimethylsiloxane copolyol as shining surfactant. In the following the non-volatile polysiloxane fluid and the shining surfactant together will be named as "hair shine agent". Several ranges, such as film thickness, g composition applied per hair etc. are given based on the amount of the non-volatile polysiloxane fluid alone. If the shining surfactant is present in the compositions the ranges given, such as film thickness, g composition applied per hair etc. apply preferably to the mixture of the "hair shine agent".

The nonvolatile polysiloxane fluid may be preferably a dimethicone and/or dimethiconol. The nonvolatile polysiloxane fluid and the shining surfactant will be intermixed in the same phase of the composition. The hair shine agent will generally be present at a level of from about 0.1% to about 15.0%, by weight of the composition, preferably from about 1% to about 12.0%, by weight of the hair care composition, more preferred from about 3.5% to about 10.0% by weight of the composition, more preferred from about 4.0% to about 8.0% by weight of the composition, most preferred from about 4.5% to about 6.5% by weight of the composition or any other numerical range which is narrower and which falls within such broader numerical range, as if such narrower numerical ranges were all expressly written herein. The hair shine agent contains the indicated essential ingredients, but it can also contain other ingredients which do not prevent the composition from functioning in its intended manner in the method as disclosed herein. The total level of the two ingredients will preferably be within the same ranges given above for the hair shine composition.

In one particular embodiment the nonvolatile polysiloxane fluid and the polydimethylsiloxane copolyol as shining surfactant will be combined in a special range in the hair shine agent. The amount of the nonvolatile polysiloxane fluid and the polydimethylsiloxanes copolyol is preferably in the range of from about 88% to about 92% polydimethylsiloxane and from about 12% to about 8% polydimethylsiloxane copolyol, preferably about 90% polydimethylsiloxane and about 10% polydimethylsiloxane copolyol or any other numerical range which is narrower and which falls within such broader numerical range, as if such narrower numerical ranges were all expressly written herein.

Non-Volatile Polysiloxane Fluid

The compositions used in the method of the present invention contain as an essential ingredient a non-volatile polysiloxane fluid, also named "silicone fluid" or "silicone oil". The term "non-volatile" as used herein means the material referred to exhibits very low or no significant vapor pressure at ambient conditions, as well-known and understood in the art. Non-volatile materials will generally exhibit no more than 0.2 mm Hg at 25° C. and one atmosphere. Non-volatile materials will also generally have a boiling point at one atmosphere of at least 275° C., preferably at least 300° C.

The polysiloxane fluid for use herein will generally have a kinematic viscosity of at least about 10 centistokes at 25° C., preferably from about 20 to about 2,000,000 centistokes, more preferred from about 30 to about 500,000 centistokes. Other viscosity non-volatile silicone fluids can also be used in the in the method of the present invention as long as the other requirements described herein are met. In general, if conditioning as well as hair shine is desired from the silicone fluid, higher viscosity materials such as those having a kinematic viscosity above about 50,000 centistokes, preferably above about 100,000 centistokes are preferably used. The kinematic viscosity can be measured by means of a glass capillary viscometer as set forth in Dow Corning Corporate Test Method CTM0004, Jul. 20, 1970.

The polysiloxane fluid suitable for purposes hereof includes those represented by general Formula (I):

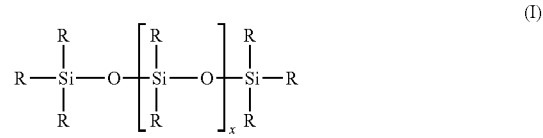

wherein each R, independently is unsubstituted aliphatic, e.g. alkyl, alkenyl or alkinyl, aryl, alkaryl, or hydrogen, or combinations thereof; and x is an integer of at least 1, typically from 1 to about 1,000.

The polysiloxane fluid can be cyclic or linear. Linear polysiloxanes are exemplified above by Formula I. Branched chain can also be used. Cyclic polysiloxanes include those represented by Formula (II):

wherein R is as defined above, n is an integer greater than 5, preferably from 6 to 10.

The substituents on the siloxane chain (R) may have any structure as long as the resulting polysiloxanes remain fluid at room temperature, are hydrophobic, are neither irritating, toxic nor otherwise harmful when applied to the hair, are compatible with the other components of the composition are chemically stable under normal use and storage conditions, are capable of being deposited on the hair, and the resulting polysiloxane fluid is still non-volatile.

Preferred alkyl, alkenyl and alkinyl substitutes are $C_1$-$C_5$ alkyls, alkenyls and alkinyls, more preferably from $C_1$-$C_4$, most preferably from $C_1$-$C_2$. The aliphatic portions of alkaryl groups can be straight or branched chains and preferably have from one to five carbon atoms, more preferably from one to four carbon atoms, even more preferably from one to three carbon atoms, most preferably from one to two carbon atoms.

The polysiloxane fluid can further be a dimethiconol. Dimethiconols include those represented by Formula (III):

Wherein n may be a number of 2 or greater.

Preferably used are linear polysiloxane fluids, in particular polydimethylsiloxane or dimethiconol, such as e.g. the 2502 fluids from Dow corning, the Silsoft EM series from Momentive, the DMF Series, the TMF series, Dimethyl Silicone Fluid KF96A and KM96H series or the KM906A series (supplied as Si/W emulsion) from Shin-Etsu Silicones, the ICM EM series from ICM products Inc., the Dimethisil DM series from Innospec Performance Chemicals or mixtures thereof. The compositions used in the method of the present invention comprise from about 0.01% to about 10.0% by weight of the composition, preferably from about 1.0% to about 8.0% by weight of the composition, more preferred from about 2.5% to about 7.0% by weight of the composition, more preferred from about 4.0% to about 6.0% by weight of the composition, more preferred from about 4.5% to about 5.5% by weight of the composition, more preferred about 4.5% by weight of the composition of the linear polysiloxane fluid, in particular polydimethylsiloxane, or any other numerical range which is narrower and which falls within such broader numerical range, as if such narrower numerical ranges were all expressly written herein.

Shining Surfactants

The compositions used in the method of the present invention further comprise preferably a shining surfactant. A "shining surfactant" as understood herein is a surfactant compound that imparts shine to the hair itself. Suitable shining surfactants are compatible with the polysiloxane fluid used herein and are suitable for application to the hair. The shining surfactant is in particular a silicone emulsifiers also known as silicone surfactant, wherein polydimethylsiloxane copolyol is preferred.

A wide variety of silicone emulsifiers is useful herein. These silicone emulsifiers are typically organically modified siloxanes, also known to those skilled in the art as silicone surfactants, in particular polyether siloxane copolymers, more particular polydimethylsiloxane copolyol is preferred, such as e.g. the KF6000 series from Shin-Etsu Silicones or the PEG Dimethicones from Dow Corning.

The preference is that any surfactant used in the composition remains fluid on the hair and does not crystallize out of the composition after drying, diffusing light and reducing the level of visual shine.

Polyether Siloxane Copolymer

Polyether siloxane copolymers, or silicone "copolyols" as they are sometimes referred to, are silicone-containing surfactants that can be used as preferred shining surfactants in the compositions disclosed herein. Silicone copolyols are surfactants characterized by a hydrophobic polysiloxane chain and a hydrophilic alkoxy portion. Silicone copolyols which may be used include polyalkylene oxide modified polydimethylsiloxanes of the following formulae IV:

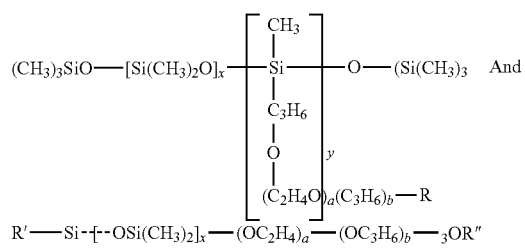

wherein R is hydrogen, an alkyl group having from 1 to about 12 carbon atoms, an alkoxy group having from 1 to about 6 carbon atoms or a hydroxyl group; R' and R" are alkyl groups having from 1 to about 12 carbon atoms; x is an integer of from 1 to 100, preferably from 20 to 30; y is an integer of 1 to 20, preferably from 2 to 10; and a and b are integers of from 0 to 50, preferably from 20 to 30.

Silicone copolyols among those useful herein are also disclosed in the following patent documents, all incorporated by reference herein: U.S. Pat. No. 4,122,029, Geen, et al., issued Oct. 24, 1978; U.S. Pat. No. 4,265,878, Keil, issued May 5, 1981; and U.S. Pat. No. 4,421,769, Dixon, et al., issued Dec. 20, 1983. Such silicone copolyol materials are also disclosed, in hair compositions, in British Patent Application 2,066,659, Abe, published Jul. 15, 1981 (incorporated by reference herein) and Canadian Patent 727,588, Kuehns, issued Feb. 8, 1966 (incorporated by reference herein). Useful silicone emulsifiers include for example dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds which contain C2-C30 pendant side chains. Still other useful dimethicone copolyols include materials having various cationic, anionic, amphoteric, and zwitterionic pendant moieties.

Suitable examples comprise dimethicone PEG-8 adipate, dimethicone PEG-8 benzoate, dimethicone PEG-7 phosphate, dimethicone PEG-10 phosphate, dimethicone PEG/PPG-20/23 benzoate, dimethicone PEG/PPG-7/4 phosphate, dimethicone PEG/PPG-12/4 phosphate, PEG-3 dimethicone, PEG-7 dimethicone, PEG-8 dimethicone, PEG-9 dimethicone, PEG-10 dimethicone, PEG-12 dimethicone, PEG-14 dimethicone, PEG-17 dimethicone, PEG/PPG-3/10 dimethicone, PEG/PPG-4/12 dimethicone, PEG/PPG-6/11 dimethicone, PEG/PPG-8/14 dimethicone, PEG/PPG-14/4 dimethicone, PEG/PPG-15/15 dimethicone, PEG/PPG-16/2 dimethicone, PEG/PPG-17/18 dimethicone, PEG/PPG-18/18 dimethicone, PEG/PPG-19/19 dimethicone, PEG/PPG-20/6 dimethicone, PEG/PPG-20/15 dimethicone, PEG/PPG-20/20 dimethicone, PEG/PPG-20/23 dimethicone, PEG/PPG-20/29 dimethicone, PEG/PPG-22/23 dimethicone, PEG/PPG-22/24 dimethicone, PEG/PPG-23/6 dimethicone, PEG/PPG-25/25 dimethicone and PEG/PPG-27/27 dimethicone. Further commercially available silicone copolyols which can be used herein, include Silwet Surface Active Copolymers (manufactured by the Union Carbide Corporation); Dow Corning Silicone Surfactants (manufactured by the Dow Corning Corporation) and ShinEtsu Emulsifying Silicones (manufactured by Shin-Etsu Chemical Co., Ltd.), such as PEG/PPG-20/22 Butyl Ether Dimethicone or PEG-32 Methyl Ether Dimethicone.

A variety of suitable non-silicone-containing organic surfactants that can be used are described below.

Secondary Surfactant

The present compositions further comprise a secondary surfactant capable of stabilizing a silicone in water emulsion. Preferred surfactants and surfactant blends for stabilizing the composition have an overall required HLB (hydrophilic lipophilic balance) in the range of 8-12. The secondary surfactant is used to stabilize the formation of the composition, but does not impart shine to the hair. A variety of suitable non-silicone-containing organic surfactants that can be used are described below, including, but not limited to nonionic, anionic, cationic or zwitterionic surfactants. Preferably, the secondary surfactant is an anionic surfactant.

Nonionic Surfactants

Nonionic surfactants which are useful in the method of the present invention can be broadly defined as including compounds produced by the condensation of alkylene oxide groups (hydrophilic in nature) with a hydrophobic compound, which may be aliphatic or alkyl aromatic in nature. Nonlimiting examples of classes of nonionic surfactants are:

1. The condensation product of aliphatic alcohols having from about 8 to about 18 carbon atoms, in either straight chain or branched chain configuration, with ethylene oxide, e.g., a coconut alcohol ethylene oxide condensate having from about 2 to about 30 moles of ethylene oxide per mole of coconut alcohol, the coconut alcohol fraction having from about 10 to about 14 carbon atom.
2. The polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 3 to about 60 moles of ethylene oxide per mole of alkyl phenol.
3. Those derived from the condensation of ethylene oxide with the product resulting from the reaction of propylene oxide and ethylene diamine products.
4. Long chain tertiary amine oxides such as those corresponding to the following general formula:

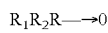

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals (the arrow in the formula represents a semipolar bond).
5. Long chain tertiary phosphine oxides corresponding to the following general formula:

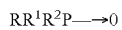

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and $R^1$ and $R^2$ are each alkyl or monohydroxyalkyl groups containing from about 1 to about 3 carbon atoms (the arrow in the formula represents a semipolar bond).
6. Long chain dialkyl sulfoxides containing one short chain alkyl or hydroxyl alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety.
7. Polysorbates, e.g., sucrose esters of fatty acids. Such materials are described in U.S. Pat. No. 3,480,616, e.g., sucrose cocoate (a mixture of sucrose esters of a coconut acid, consisting primarily of monoesters, and sold under the tradenames GRILLOTEN LSE 87K from RITA, and CRODESTA SL-40 from Croda).
8. Alkyl polysaccharide nonionic surfactants are disclosed in U.S. Pat. No. 4,565,647. Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group. The polysaccharide can contain from about 1.0 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units. Optionally there can be a polyalkyleneoxide chain joining the hydrophobic moiety and the polysaccharide moiety. The alkyl group preferably contains up to about 3 hydroxy groups and/or the polyalkyleneoxide chain can contain up to about 10, preferably less than 5, alkylene moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses and/or galactoses.
9. Polyethylene glycol (PEG) glyceryl fatty esters, as depicted by the formula $RC(O)OCH_2CH(OH)CH_2(OCH_2CH_2)_nOH$ wherein n is from about 5 to about 200, preferably from about 20 to about 100, more preferably from about 30 to about 85, and RC(O)— is an ester wherein R comprises an aliphatic radical having from about 7 to about 19 carbon atoms, preferably from about 9 to 17 carbon atoms, more preferably from about 11 to 17 carbon atoms, most preferably from about 11 to about 14 carbon atoms. The combinations of n from about 20 to about 100, with $C_{12}$-$C_{18}$, preferably $C_{12}$-$C_{15}$ fatty esters, for minimized adverse effect on foaming, is preferred.

Anionic Surfactants

Anionic surfactants useful herein include alkyl and alkyl ether sulfates. These materials typically have the respective formulae $ROSO_3M$ and $RO(C_2H_4O)_xSO_3M$, wherein R is alkyl or alkenyl of from about 10 to about 20 carbon atoms, x is 1 to 10, and M is a water-soluble cation such as ammonium, sodium, potassium and triethanolamine.

Another suitable class of anionic surfactants are the water-soluble salts of the organic, sulfuric acid reaction products of the general formula:

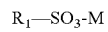

wherein $R_1$ is chosen from the group consisting of a straight or branched chain, saturated aliphatic hydrocarbon radical having from about 8 to about 24, preferably about 12 to about 18, carbon atoms; and M is a cation Important examples are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12-18}$ n-paraffins.

Additional examples of anionic surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids for example, are derived from coconut oil. Other anionic surfactants of this variety are set forth in U.S. Pat. Nos. 2,486,921; 2,486,922; and 2,396,278.

Still other anionic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Other suitable anionic surfactants utilizable herein are olefin sulfonates having about 12 to about 24 carbon atoms. The term "olefin sulfonate" is used herein to mean compounds which can be produced by the sulfonation of a-olefins by means of uncomplexed sulfur trioxide, followed by neutralization of the acid reaction mixture in conditions such that any sultones which have been formed in the reaction are hydrolyzed to give the corresponding hydroxyl-alkanesulfonates. The a-olefins from which the olefin sulfonates are derived are mono-olefins having about 12 to about 24 carbon atoms, preferably about 14 to about 16 carbon atoms. Another class of anionic organic surfactants are the b-alkyloxy alkane sulfonates. If anionic surfactants are used their amount is small enough to be not effective as cleansing surfactant.

Cationic Surfactants

Cationic surfactants useful in compositions used in the method of the present invention, particularly as additional conditioner actives or as components in gel vehicles, contain amino or quaternary ammonium hydrophilic moieties which are positively charged when dissolved in the aqueous composition used in the method of the present invention. Cationic surfactants among those useful herein: are disclosed in the following documents, all incorporated by reference herein; M.C. Publishing Co., McCutcheon's Detergents & Emulsifiers, (North American edition 1979); Schwartz, et al., Surface Active Agents, Their Chemistry and Technology, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983.

Among the quaternary ammonium-containing cationic surfactant materials useful herein are those of the general formula V:

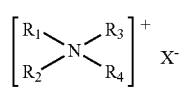

(V)

wherein $R_1$-$R_4$ are independently and aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups. The longer chain aliphatic groups, e.g., those of about 12 carbons, or higher, can be saturated or unsaturated.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E. O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soy amine chloride, stearylamine formate, N-tallowpropane diamine dichloride and stearamidopropyl dimethyl amine citrate. Cationic amine surfactants included among those useful in the present invention are disclosed in U.S. Pat. No. 4,275,055, Nachtigal, et al., issued Jun. 23, 1981, incorporated by reference herein.

A particular category of quaternary ammonium cationic conditioning agent that can be useful herein is characterized by the formula VI:

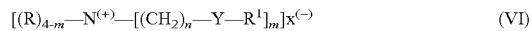

$$[(R)_{4-m}-N^{(+)}-[(CH_2)_n-Y-R^1]_m]X^{(-)}$$ (VI)

wherein each R substituent is a short chain $C_1$-$C_6$ alkyl or hydroxyalkyl group, benzyl, or mixtures thereof; each m is 2 or 3; each n is from 1 to about 4; each Y is —O—(O)C—, or —C(O)—O—; each $R_1$ is a hydrocarbyl, or substituted hydrocarbyl, group, the sum of carbons in each R', plus one when Y is —O—(O)C—, being $C_{12}$-$C_{22}$; the average Iodine Value of the parent fatty acid of the $R^1$ group being from about 60 to about 140; and wherein the counterion, $X^-$ is any compatible anion.

Zwitterionic Surfactants

Zwitterionic surfactants, useful in shampoos as well as conditioners, are exemplified by those which can be broadly described as derivatives of aliphatic quaternary ammonium, phosphonium, and sulfonium compounds, in which the aliphatic radicals can be straight or branched chain, and where one of the aliphatic substitutes contains from about 8 to about 18 carbon atoms and one contains an anionic water-solubilizing group, e.g. carboxy, sulfonate, sulfate, phosphate, or phosphonate. A general formula for these is formula VII:

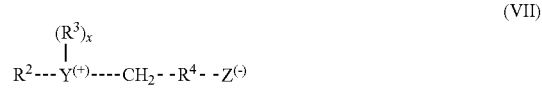

(VII)

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionics such as betaines are also useful in the present invention. Examples of betaines useful herein include the high alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxy ethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like, amidobetaines and amidosulfobetaines, wherein the RCONH(CH$_2$)$_3$ radical is attached to the nitrogen atom of the betaine are also useful in this invention. If zwitterionic surfactants are used herein their amount is small enough to be not effective as cleansing surfactant.

Rheology Modifier

The hair care composition as disclosed herein preferably comprises a rheology modifier. Several groups of rheology modifiers are known in the art. The rheology modifiers used herein shall not only modify the viscosity of the composition, but must not affect the shining imparted to the hair after the composition has been applied thereto. In addition, the rheology modifier used herein shall stabilize the formation of the oil-in-water emulsion. Surprisingly, it was found that rheology modifiers comprising an acrylic acid/Vinyl ester copolymer meet the requirements mentioned before. Emulsions comprising an acrylic acid/Vinyl ester copolymer are more stable over time compared to emulsions without the rheology modifier. Further, the acrylic acid/Vinyl ester copolymer only shows a slight negative impact on the shining effect over the amounts disclosed herein. Separation time was measured by 25° C. and 40° C. simulation accelerated aging. Emulsions comprising an acrylic acid/Vinyl ester copolymer were stable with no visual signs of separation over >3 month at 40° C. Emulsions without an acrylic acid/Vinyl ester copolymer separate immediately or latest within 24 hours after preparation and have to be emulsified again before use by shaking.

Rheology modifiers comprising the acrylic acid/Vinyl ester copolymer, in particular the acrylates/vinyl isodecanoate crosspolymer are provided e.g. by 3V Sigma SPA under the tradename "Stabylene 30". Preferably, the acrylates/Vinyl isodecanoate crosspolymer "Stabylene 30" is used as rheology modifier for emulsions as disclosed herein.

Preferably the compositions used in the method of the present invention comprises from about 0.003%, from about 0.05% or from about 0.1% to about 0.6% by weight of the composition of the rheology modifier, more preferred the present compositions comprise from about 0.2% to about 0.5% by weight of the composition, more preferred about 0.5% by weight of the composition of the rheology modifier, or any other numerical range which is narrower and which falls within such broader numerical range, as if such narrower numerical ranges were all expressly written herein. If the rheology modifier is used above the indicated level, the viscosity of the composition increases significantly.

Other Ingredients

The compositions used herein can also contain other ingredients suitable for use as carriers or vehicles for the composition, as well as other active ingredients in addition to the essential active ingredients discussed above. Choice of appropriate additional carrier ingredients will depend on the particular polysiloxane fluid to be used, and the particular type of composition that is desired. A suitable combination of additional ingredients might be for examples preservatives, a buffer, fragrances, antioxidants, colorants, organic acids, a solvent, humectants, emollients, preferably volatile polysiloxane fluids and/or water and/or combinations thereof. The choice and formulation of such products is well within the ambit of those of ordinary skill in the art. Nonlimiting, exemplary additional ingredients are further described below. In the present composition only additional ingredients are used which do not have any negative effect to the shine imparted to the hair.

Carrier

Suitable additional carrier fluids for use in the present invention include, but are not limited to lower alcohols such as isopropanol, hydrocarbons (such as isobutane, hexane, decene, acetone), halogenated hydrocarbons (such as Freon), linalool, hydrocarbon esters (such as ethyl acetate, dibutyl phthalate), volatile hydrocarbons and silicone fluids and/or derivatives, especially siloxanes, such as cyclomethicone and dimethicone (having for example, viscosity at 25° C. of about 15 centipoise or less), and mixtures thereof. Although, the composition might comprise lower alcohols as carrier fluids, the compositions are free of ethanol in order to avoid the drawbacks associated with ethanol, such as drying out the scalp and/or the hairs, promoting flaking and imparting negative sensations, such as itchy skin feeling.

Water

The compositions used in the method of the present invention will comprise water, generally at a level of from about 79.5% to about 99.5%, by weight of the composition, preferably from about 90.0% to about 97.5%, more preferred from about 92.0% to about 95.0% or any other numerical range which is narrower and which falls within such broader numerical range, as if such narrower numerical ranges were all expressly written herein.

The compositions herein can contain a variety of other optional components suitable for rendering such compositions more cosmetically or aesthetically acceptable or to provide them with additional usage benefits. Such optional ingredients generally are used individually at levels of from about 0.01% to about 10.0%, preferably from about 0.05% to about 5.0%, of the composition. Such conventional optional ingredients are well known to those skilled in the art:

pH adjusting agents, such as citric acid, sodium citrate, succinic acid, phosphoric acid, sodium hydroxide, sodium carbonate; salts, in general, such as potassium acetate and sodium chloride. The pH of the present compositions generally will be from about 3 to about 9, preferably from about 4 to about 8, more preferred from about 5 to about 7.

Preservatives, such as benzyl alcohol, methyl paraben, propyl paraben, imidazolidinyl urea, phenoxyethanol and ethylhexylglycerin or mixtures thereof.

Antioxidants/ultra violet filtering agents, such as octyl methoxycinnamate, benzophenone-3 and DL-alpha tocopherol acetate.

Coloring agents, such as any of the FD&C or D&C dyes; hair oxidizing (bleaching) agents, such as hydrogen peroxide, perborate and persulfate salts; hair reducing agents, such as the thioglycolates.

Opacifiers, such as polystyrene.

Pearlescent aids, such as ethylene glycol distearate (which is also a suspending agent and can be used to suspend insoluble materials in the compositions).

Fragrances and sequestering agents, such as tetrasodium ethylenediamine tetra-acetate; sensates such as those that chemically stimulate the nerve endings to induce a perception of cooling, heat, or other sensation of change in conditions when applied to the skin, e.g., camphor, menthol, 1-isopulegol, ethyl menthane carboxamide and trim ethyl isopropyl butanamide, and others including but not limited to those disclosed in GB-B-1315626, GB-B-1404596 and GB-B-1411785, all incorporated by reference.

Anti-dandruff agents, such as zinc pyrithione, piroctone olamine, ketoconazole, climbazole, salicylic acid.

Polymer plasticizing agents, such as glycerin, disobutyl adipate, butyl stearate, and propylene glycol.

mica, and mother of pearl

And combinations thereof, whereas the composition should not contain components which unduly interfere with the performance of the composition.

Scalp Conditioning Agents

The compositions may comprise a scalp conditioning agent which is in addition to the hair shine agent and can condition the skin of the scalp and thus reduce or eliminate any drying-out effect of the scalp. The scalp conditioning agent will preferably be present at a level of from about 0.1% to about 10.0%, by weight of the composition, more preferably from about 0.25% to about 5.0%, most preferably from about 0.5% to about 3.0% or any other numerical range which is narrower and which falls within such broader numerical range, as if such narrower numerical ranges were all expressly written herein.

The scalp conditioning agent hereof can be any material which is suitable for conditioning skin that can provide emolliency, moisturization, or both, to the scalp and can be incorporated into the compositions hereof without preventing the compositions hereof from enhancing shine to the hair. Thus the scalp conditioning agents hereof include both skin emollients and skin humectants and combinations thereof. Emollients can include conventional lipids (e.g. esters such as fats, oils, waxes and the like), polar lipids (e.g. lipids that have been hydrophilically modified to render them more water soluble), silicones, and hydrocarbons. For example scalp conditioning agents as mentioned at pages 27-32 and 46-48 in "Cosmetic Bench Reference", 1994 Edition, incorporated herein by reference. Emollients can be included in the shine composition as long as they do not reduce the level of shine or increase the film thickness to cause bridging.

The hair care compositions used in the method of the present invention can be made using conventional formulation and mixing techniques. Exemplary methods of making various types of cosmetic compositions are also described more specifically in the Examples below.

Any of a variety of conventional packages for the hair care products can be used, as is previously discussed. Selection of spray packages, including aerosols and non-aerosols, which will provide the required particle size distribution for sprays in accordance with the present invention is well within the ambit of one of ordinary skill in the hair spray art. Aerosol hair sprays additionally utilize a propellant which can be intermixed with the composition itself or be separately incorporated into the package. Examples of propellants include, but are not limited to trichlorofluoromethane, dichlorodifluoromethane, difluoroethane, dimethylether, propane, n-butane or isobutane. The level of propellant can be adjusted as desired but is generally used at a level of from about 5.0% to about 50.0%, by weight, of the aerosol hair spray compositions.

Suitable spray containers are well known in the art and include conventional, non-aerosol pump sprays i.e. "atomizers", aerosol containers or can having propellant, as described above, and also pump aerosol containers utilizing compressed air as the propellant. Pump aerosol containers are disclosed, for example, in U.S. Pat. No. 4,077,441, Mar. 7, 1978, Olofsson and 4,850,577, Jul. 25, 1989, TerStege, both incorporated by reference herein, and also in U.S. Ser. No. 07/839,648, Gosselin, Lund, Sojka, and Lefebvre, filed Feb. 21, 1992, "Consumer Product Package Incorporating A Spray Device Utilizing Large Diameter Bubbles".

EXPERIMENTAL

Particle Size

The compositions to be sprayed comprise particles having a particle size. The particles are droplets comprising the hairstyling formulation. The droplet particle size is determined by laser diffraction, such as with a Malvern 30 Instruments 2600C particle size analyzer or equivalent. The intensity of light scattered as a laser beam passes through a composition is measured. This data is then analyzed to calculate the size of the particles that created the scattering pattern. The measurement is performed using the International Organization for Standardization (ISO) Standard Method ISO/WD 13320.

Film Thickness

Figure 1B:
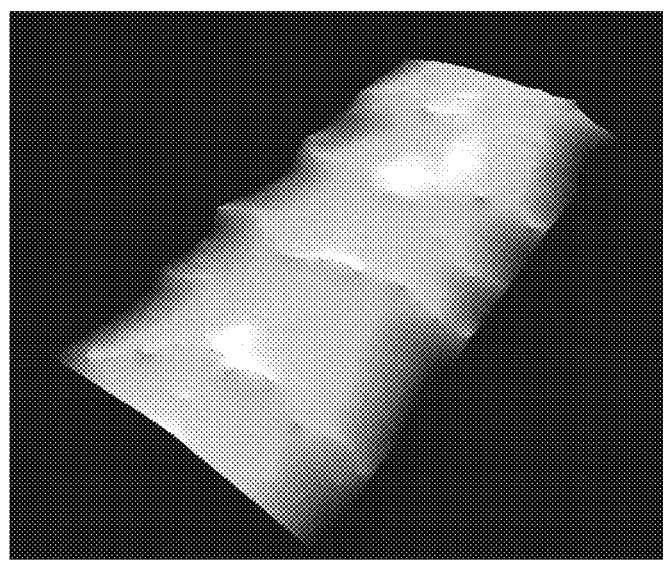
FIG. 1B shows a 3D laser image of a hair fiber after being treated with about 4 g of the composition of Example M.

FIG. 1 show a 3D laser image of a hair fiber in order to determine the film thickness of the shine agent film on the hair fiber. Hair probes (Medium Brown Hair Switch) used were supplied by International Hair Importers. The hair fibers were treated with the composition of Ex. M 1.6 g (8 pumps of 0.2 g) (FIG. 1A) or 4 g (20 pumps of 0.2 g) (FIG. 1B), of the composition of Ex. M were applied to 8 inch (about 4 g) dry hair by spraying with a mean droplet size of about 70 μm. After drying images were collected with a 3D laser microscope. 3D LSM Measurements were made with a Keyence VK-X200 3D Laser Scanning Confocal Microscope consisting of a VK-X210 Measurement Unit and a VK-X200K Controller. The microscope is equipped with a VK-S105 motorized stage and is mounted on a Herzan TS-150 vibration isolation table. Images were collected with 50× and 150× objective lenses using a z-pitch ranging from 0.05 to 0.1 micrometers. Data was collected using VK Viewer version 2.2.0.0 (Keyence) and analyzed using VK Analyzer, version 3.3.0.0 (Keyence).

AFM was used to measure the average film thickness. AFM data was collected using an Asylum Model MFP-3D with the Stand Alone Base. Instrument was supported on Herzan TS-150 vibration isolation table in Herzan AEK 20021W 2002-1 isolation enclosure. Probe type was Olympus AC160 (lot 9C3002) silicon diving board. Cantilever length is 160 nm; nominal radius for a new tip is less than 15 nm Probes were calibrated for force measurements. Film thickness measures were collected in tapping (intermittent contact) mode with a Field of View (FOV) of 40×20 mm and 512×256 pixels, yielding a spatial resolution of 78 nm Image tilt was corrected with a first order plane fit. Force Maps were collected over the same areas imaged by AFM. Maps consisted of an array of 10 by 10 individual force curves uniformly distributed over the FOV.

FIG. 1A shows the hair shine agent film on a hair fiber in the range of about 200-300 nm as confirmed by AFM. FIG. 1B shows the hair shine agent film on a hair fiber >500 nm. The reason the surface of the hair fiber is more textured in FIG. 1B as opposed to FIG. 1A is the film thickness of the hair shine agent increases beyond 500 nm fluid bridges begin to form between hair fibers creating the appearance of greasy. It can be seen that hair shine agent films >500 nm become an irregular appearance resulting in the visual appearance of grease.

Silicone Bridging

FIG. 2 show a 3D LSM image of two hair fibers with an average silicone film thickness >500 nm as measured by AFM. The fibers analyzed were from the same sample than those used for FIG. 1B. After drying 3D LSD image was collected with 50× objective. 3D LSM measurements were made with a Keyence VK-X200 3D Laser Scanning Confocal Microscope consisting of a VK-X210 Measurement Unit and a VK-X200K Controller.

Figure 2A:
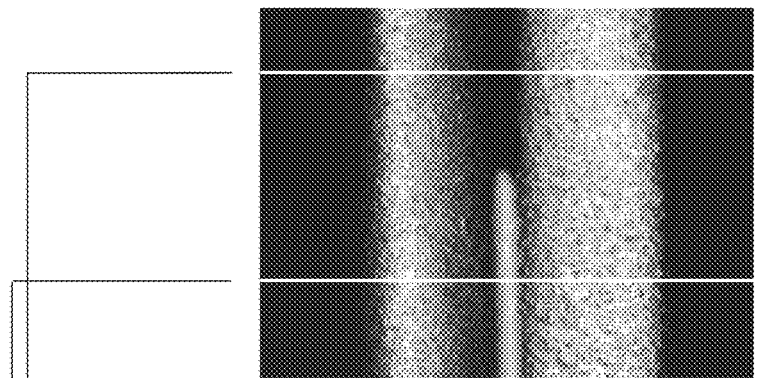
FIG. 2A shows a 3D LSM image of two hair fibers having regions without a silicone bridge and with a silicone bridge.
Figure 2B:
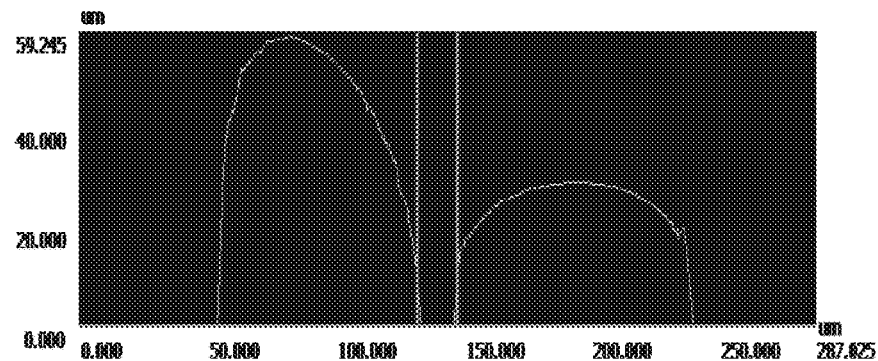
FIG. 2B shows the height data in a horizontal cut across the image shown in FIG. 2A at the region without bridging.

FIG. 2A shows the two fibers having a region without a silicone bridge and with a silicon bridge. Height data are shown in horizontal cuts across image in FIGS. 2B and 2C, display the difference between regions with bridging (FIG. 2C) and without bridging (FIG. 2B).

Figure 2C:
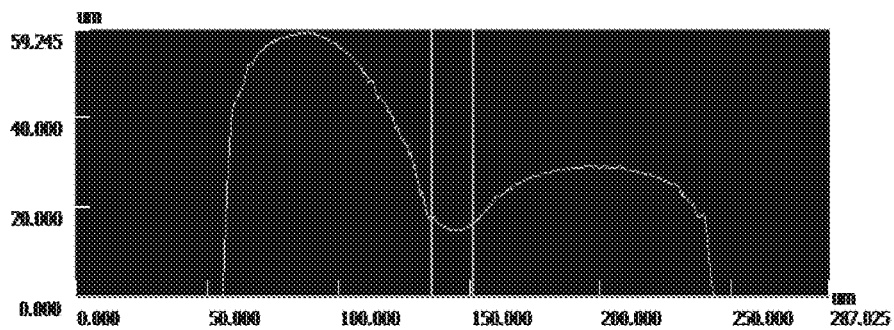
FIG. 2C shows the height data in a horizontal cut across the image shown in FIG. 2A at the region with bridging.

In region without bridging (FIG. 2B) surface profile goes to baseline between hair shafts. That means there is no material present between the hair shaft. In region with bridging (FIG. 2C) profile does not go to baseline i.e. there is silicone material present between the hair shafts. The silicone bridge between the hair fibers in FIG. 2C is about 15 μm wide.

Reich-Robbins Luster Value

For the measurement of the Reich-Robbins luster value ($L_{Reich-Robbins}$) hair with following characteristics was utilized:

Hair Tress Description

Hair tresses described below are used to calibrate instrumental exposure settings and for the measurement of the Reich-Robins luster values:
a) Medium Brown Hair Switch with 9 inch total length glued and taped at end with round configuration and 8 inch of hair (product application area) weights about 4.0 g supplied by International Hair Importers.
b) The hair with characteristics described in point a) above is oxidized by treating with bleach solution of pH 10 heated to 25° C. for approximately 30 minutes. The hair is then rinsed, washed with clarifying shampoo, fan dried and equilibrated at room temperature for at least 24 hours before any further treatment or measurement. The resulting hair had a water contact angle of 95°±5° measured as disclosed below, and color that corresponds to the following L a b values as L=35±1, a=10±1, b=20±1 respectively measured as outlined in point c) below:
c) The L a b values were measured using hand held Konica Minolta Spectrophotometer CM-2600d, with aperture diameter of 11 mm. The instrument was set at the following internal conditions for the L a b measurements: D65 (Angle light source), 10° observer and 0% UV. Position of the instrument was held perpendicular to the hair fibers while making the measurements.

Figure 3A:
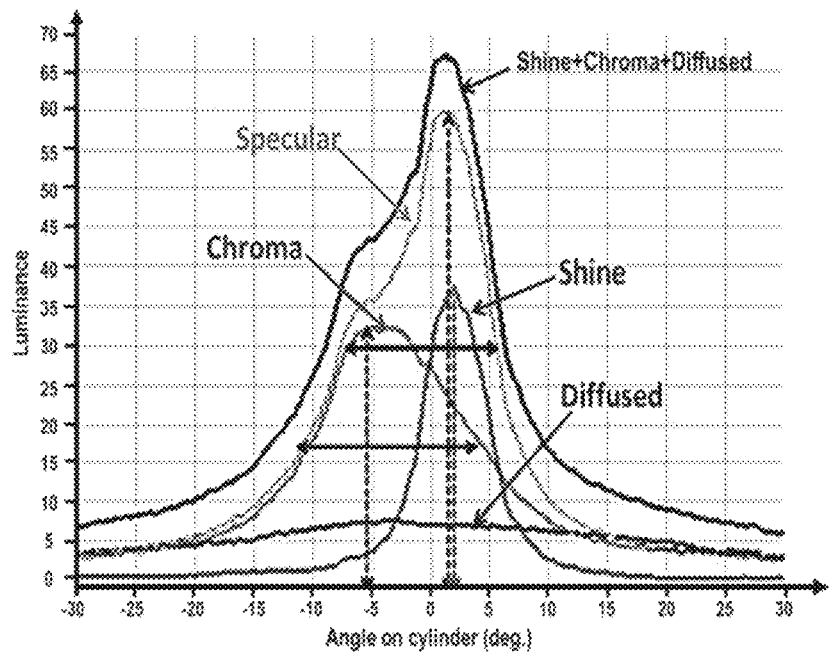
FIG. 3A shows the interaction of light with hair after hair was washed with clarifying shampoo and then dried with blow dryer without further treatment; the different parts of light reflection are shown in one diagram.

Hair tresses as described in Hair Tress Description section were washed with clarifying shampoo and then dried with blow dryer without further treatment (FIG. 3A). Then another set of hair tresses with the same characteristics was washed with clarifying shampoo and treated with the composition of Ex. M (FIG. 3B). 0.4 g of composition of Ex. M was applied to 4 g wet hair by spraying with a mean droplet size of about 70 μm. After drying with blow dryer the interaction of light with the hair fibers was measured using an imaging system, supplied by Bossa Nova Technologies, that consists of a polarized illumination, polarization camera and a cylinder on which the hair sample is mounted. This set up allows for computing separate angular distributions of intensity, shine, chroma and diffused components of the light.

Figure 3B:
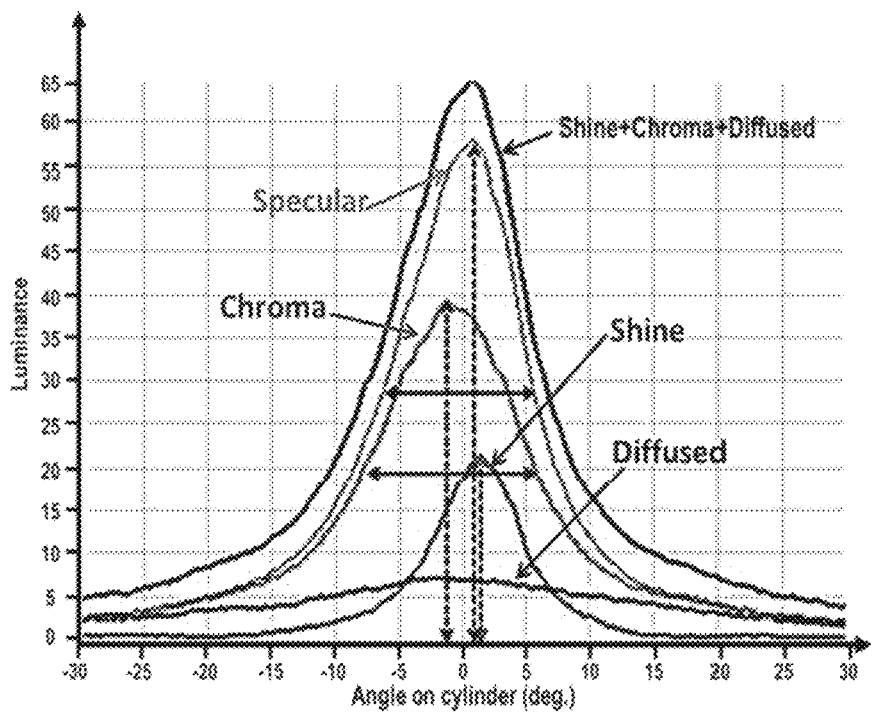
FIG. 3B shows the interaction of light with hair after hair was washed with clarifying shampoo, then dried with blow dryer and treated with composition of Example M; the different parts of light reflection are shown in one diagram.

FIG. 3 show the graphs representing the different parts of light. Shine of washed hair without any further treatment (as shown in FIG. 3A) comprises a greater shine band compared to the chroma band. In particular the maximum of the chroma band is smaller than the maximum of the shine band and is shifted to the left. After application of the composition of Ex. M (as shown in FIG. 3B) the ratio between the shine band and the chroma band has switched and the overlap between the two bands has increased. Without being bound to a theory it is believed that the hair shine composition is filling in the cuticle, causing a shift in the chroma band so that the chroma band and the shine band now overlap. The maximum of the chroma band distribution is greater than the maximum of the shine band distribution and the two maxima in FIG. 3B are closer to each other than in FIG. 3A. The quality of shine or visual appearance, calculated using Reich-Robbins luster formula, with the parameters shown in graph shown in FIG. 3B is considered more brilliant and homogeneous for the human eye than the shine appearance with a graph shown in FIG. 3A.

The Reich-Robbins luster value can be calculated from the data achieved according to the following formula:

$$L_{Reich-Robbins} = S/D * \Theta_{1/2}$$

Wherein S is the total amount (integral) of the specular light, D is the total amount (integral) of the diffused light and $\Theta_{1/2}$ the width of the specular light distribution.

Thermal Protection

The polysiloxane fluid mixture as disclosed in Table IV Ex. M was tested for thermal protection. The hair switches used were the same as described above. For each hair switch, the bottom inch was cut from the switch and discarded. The new end of the hair switch was clipped to about 1 mm in length and placed in a vial. For each vial, two DSC (differential scanning calorimetry) pans were prepared with 6-12 mg hair and 50 μL distilled water then sealed. A DSC scan was run on each pan with an empty pan as a reference. The instrument was equilibrated at 90° C., then ramped up in temperature by 5° C./minute, to a final temperature of 200° C. The instrument used for the DSC scan was from TA Instruments, model 2920 DSC. The DSC pans used were a high volume/high pressure pan available from Texas Instruments part number 900825.902.

The denaturation temperatures were determined and averaged from the resulting curves. A positive delta in denaturation temperature from control denotes thermal protection. The higher the $T_{dp}$ (denaturation temperature), the greater the thermal protection. As can be seen by the Table I below, application of emulsion of Ex. M compares favorably with hair not exposed to heat. Thus, the application of emulsion of Ex. M shows a heat protection benefit.

TABLE I

| Samples | Treatments to 4 g/8" hair | Denaturation Temp (° C.) | Loss/Gain in Temperature (° C.) |
|---|---|---|---|
| Control No Product | No Heat applied from Flat iron | 148.17 | Not applicable |
| | Heat Applied from Flat iron (2 cycles-30 strokes-2 cm/sec at 410 F.) | 144.35 | −3.82 |
| Composition of Ex. M | Heat Applied from Flat iron (2 cycles-30 strokes-2 cm/sec at 410 F.) | 148.12 | 3.77 |

Combing Force

The combing force measurement is a measurement of conditioning and detangling. The polysiloxane emulsion according to Ex. C was tested for combing force as a solution in water. The amounts dosed per gram hair are indicated in the table below. The hair switches used were the Medium Brown hair switches as described previously, using a 4 g/8 inch hair switch, with 3 replicates per treatment. The hair switches were pre-wet and hung to dry at 73° F./45% relative humidity overnight.

After drying overnight, the hair switches were mounted on frame that holds two combs and the top is attached to the load cell of the Instron machine. The combs pass through the hair, and the combing force is measured. A suitable instrument is an Instron Tester Instrument 5564, using Instron Merlin/Series IX Software. (Instron Inc, Canton Mass., USA).

As can be seen by the results shown in Table II below the dry combing force is reduced, i.e. hair is conditioned and detangled, upon treatment with the emulsion of Ex. C compared to several commercially available products.

TABLE II

| Products tested | Dosage | grams combing force |
| --- | --- | --- |
| Bumble & bumble Hairdresser's Invisible Oil (Commercial Shine Product 1) | 0.1 g/g hair | 102 |
| Garnier Fructis Style brillantine shine glossing spray (Commercial Shine Product 2) | 0.1 g/g hair | 96 |
| Wella Mirror Polish (Commercial Shine Product 3) | 0.1 g/g hair | 87 |
| John Frieda Fizz ease 100% Shine Glossing Mist (Commercial Shine Product 4) | 0.1 g/g hair | 70 |
| Shine Composition of Example C | 0.1 g/g hair | 42 |

Frizz Assessment Method

The polysiloxane emulsions were tested for the frizz assessment. The hair switches used were the Medium Brown hair switches as described previously, using a 4 g/8 inch hair switch, with 3 replicates per treatment. Hair was shampooed with a silicone free volumizing shampoo, rinsed, and 0.1 g/g hair of polysiloxane emulsion of Ex. Y or Z were applied to hair using a spray pump. The hair switches were air dried for 30 minutes, then blow dried until no detectable moisture was present. The hair switches were then conditioned at 80F at 80% relative humidity for 2 hours. Frizz assessment was performed by visual comparison, where hair treated with emulsion of Ex. Y or Z were shown to have less frizz than control hair (no treatment).

Hair Contact Angle Determination

The Hair Contact Angle determination as used herein uses the method developed by Franz J. Wortmann, Gabriele Wortmann, and Erik Schulze zur Wiesche published in Langmuir 2010, 26(10), 7365-7369. The measurement uses the principles of the Wilhelmy measurement on a hair fiber. To measure the dynamic wetting force, the fiber is suspended underneath a microbalance with its root end pointing downward. With the water surface moving upward, the fiber proceeds through the water surface. This generates a force reading, which due to buoyancy decreases linearly with penetration depth. Linear regression and extrapolation to zero give the value for the Wilhelmy force (Fw), which is related to the contact angle, $\theta$ through: $Fw=L_{\sigma L} \cos \theta$, where L is the wetted perimeter of the fiber at the air/liquid interface, $\sigma L$ is the surface tension of the liquid, and $\theta$ is the contact angle. The testing conditions were the following:

Hair segments in the length range of about 20 mm and originating from near the scalp, were investigated. Measurement (Kruss Tensiometer K100 SF, Kruss, Hamburg, Germany) conditions were 20±1C and 50±4% relative humidity Immersion speed was generally 0.2 mm/min to achieve a spatial resolution in the region of 100 μm Immersion lengths employed were 5 mm for each hair. Substantial restrictions applied to the number of successfully tested fibers due to (1) the problem of buckling of the hydrophobic fibers in the advancing mode, in accordance with the considerations by Lodge, R. A. and Bushan, B. J. Appl. Polym. Sci. 2006, 102, 5255-5265, as well as due to (2) the experimental time required for long fiber segments. Significant signal noise is integral part of the experimental curves through the higher wettability of the frontal edges of the cuticle scales that are prone to mechanical and chemical damage. This effect is minimized, however, by using the advancing mode only and by immersing the fiber in the root-to-tip direction, where the cuticle scale edges point upward. Furthermore, the measurement yields the mean wetting force for the complete fiber circumference, consisting of multiple cuticle cells. This is expected to further contribute to the noise level of the signal. Circumference of hair was optically measured with camera and sufficient magnification to enable the determination of the diameter through calibrated distance measurements. The following factors may interfere with results: (1) Dirt or other environmental contamination not normally associated with hair. Contact angles are very sensitive to surface contamination; (2) curved test surface such that angles are difficult or impossible to measure; and (3) low humidity (<40% RH) when water is the test liquid such that the contact angle changes rapidly due to evaporation.

The raw wetting force data of 100 μm spacing were collected and processed as following: The first 200 μm were ignored to avoid bias from the damaged tip. Kruss software (version 3.2) along with inputs from optical determinations of the hair fiber diameter was used to determine contact angles.

Influence of the Rheology Modifier to pH-value, Viscosity and Reich-Robbins-Luster value For the level studies compositions were prepared comprising 8 different levels (0.1%, 0.2%, 0.3%, 0.4%, 0.5%, 0.6%, 0.7% and 0.8%) of acrylates/vinyl isodecanoate crosspolymer provided e.g. by 3V Sigma SPA under the tradename "Stabylene 30" as rheology modifier. The polysiloxane fluid (0.45% dimethicone (DMF/PDMS)) and the shining surfactant (0.05% dimethicone copolyol) were premixed and added to the carrier (0.49% SLS, 0.02% citric acid, 1.45% preservatives, 0.2% perfume, 0.04-0.24% 2-Amino-2-methyl-1-propanol (AMP)). Then the 8 different amounts of the rheology modifier were added and pH-value, viscosity and Luster value of the compositions were measured. Table III shows the results:

TABEL III

| Rheology modifier | pH value | Viscosity (Pa * s) | RR-Luster value |
| --- | --- | --- | --- |
| 0.1 | 4.55 | 0 | 47.9 |
| 0.2 | 4.73 | 0.326 | 46.9 |
| 0.3 | 4.86 | 1.689 | 46.5 |
| 0.4 | 5.11 | 1.993 | 46.8 |
| 0.5 | 5.12 | 4.034 | 44.7 |
| 0.6 | 5.12 | 6.717 | 47.4 |
| 0.7 | 5.01 | 12.036 | 45.6 |
| 0.8 | 4.88 | 13.060 | 44.3 |

Examples

The following examples further illustrate preferred embodiments to be used within the scope of the present invention. The examples are given solely for the purposes of illustration and are not to be construed as limitations of the present invention as many variations of the invention are possible without departing from its spirit and scope. Tables VI to VI show several example embodiments.

TABLE IV

| Compounds | Ex. A | Ex. B | Ex. C | Ex. D | Ex. E | Ex. M | Ex. I |
|---|---|---|---|---|---|---|---|
| Dimethicone (DMF/PDMS) | 4.5% | — | 4.5% | 4.5% | 4.5% | 4.5% | 2.25% |
| Dimethicone copolyol | 0.5% | — | 0.5% | 0.5% | 0.5% | 0.5% | 0.25% |
| Acrylates/Vinyl Isodecanoate Crosspolymer | 0.2% | 0.2% | 0.4% | 0.6% | 0.8% | — | — |
| Surfactant (SLS) | 0.49% | — | 0.49% | 0.49% | 0.49% | 0.49% | 0.245% |
| Citric acid | 0.02% | — | 0.02% | 0.02% | 0.02% | 0.02% | 0.01% |
| preservative | 1.45% | 1.4% | 1.45% | 1.45% | 1.45% | 0.05% | — |
| perfume | 0.2% | 0.2% | 0.2% | 0.2% | 0.2% | — | — |
| 2-Amino-2-methyl-1-propanol (AMP) | 0.08% | 0.08% | 0.09% | 0.13% | 0.24% | — | — |
| water | QS to 100 | QS to 100 | QS to 100 | QS to 100 | QS to 100 | QS to 100 | QS to 100 |

TABLE V

| Compounds | Ex. F | Ex. G | Ex. H | Ex. J | Ex. K | Ex. L |
|---|---|---|---|---|---|---|
| Dimethicone (DMF/PDMS) | 4.5% | 4.5% | 2.5% | 5.5% | 7.0% | 10.0% |
| Dimethicone copolyol | 0.5% | 0.5% | 0.3% | 0.45% | 0.8% | — |
| PEG/PPG-20/22 Butyl Ether Dimethicone | 0.5% | 0.5% | 0.2% | 0.65% | 0.2% | 1.0% |
| Acrylates/Vinyl Isodecanoate Crosspolymer | 0.02% | — | — | 0.5% | — | — |
| Surfactant (SLS) | 0.49% | 0.49% | — | — | — | — |
| Citric acid | 0.02% | 0.02% | 0.02% | 0.02% | 0.02% | — |
| preservative | 1.45% | 1.45% | 1.45% | 1.0% | 0.5% | 1.0% |
| perfume | 0.2% | 0.2% | 0.5% | — | — | 0.2% |
| AMP | 0.08% | — | — | 0.1% | — | — |
| water | QS to 100 | QS to 100 | QS to 100 | QS to 100 | QS to 100 | QS to 100 |

TABLE VI

| Compounds | Ex. N | Ex. O | Ex. P | Ex. Q | Ex. R | Ex. S | Ex. T | Ex. X | Ex. Y | Ex. Z |
|---|---|---|---|---|---|---|---|---|---|---|
| Dimethicone (DMF/PDMS) | 4.50% | 5.00% | — | — | — | — | 4.50% | 5.00% | 4.50% | 4.50% |
| Dimethiconol | — | — | 15.00% | 10.00% | 5.00% | 10.00% | — | 5.00% | | |
| Dimethicone copolyol | — | — | — | — | — | — | — | — | 0.50% | 0.50% |
| Triethanolamine dodecylbenzene sulfonate | — | 0.50% | 1.00% | 0.05% | 0.50% | — | — | — | — | — |
| Sodium Dodecylbenzene sulfonate | — | — | — | 1.00% | — | 1.00% | — | — | — | — |
| Polyethylene lauryl ether | — | 1.00% | 1.00% | — | — | — | — | — | — | — |
| Trideceth-4 | — | — | — | — | 0.50% | — | — | — | — | — |
| Octamethyl cyclotetrasiloxane | — | 0.50% | 0.50% | 0.50% | — | 0.05% | — | — | — | — |
| alkylbenzene sulfonic acid | — | 0.50% | 0.50% | 1.00% | 1.00% | — | — | — | — | — |
| polyethylene glycol alkyl ether | — | — | — | — | 0.50% | 0.50% | — | — | — | — |
| Tridecanolethoxylate, branched | — | — | — | 0.05% | — | 0.10% | — | — | — | — |
| Laureth 23 | 0.50% | — | — | — | — | — | — | — | — | — |
| Laureth 4 | 0.50% | — | — | — | — | — | — | 0.50% | — | — |
| Acrylates/Vinyl Isodecanoate Crosspolymer | 0.20% | 0-0.2% | 0-0.2% | 0-0.2% | 0-0.2% | 0-0.2% | 0.20% | 0.50% | — | — |
| Phytosteryl/Octyldodecyl Lauroyl Glutamate | — | — | — | — | — | — | — | — | 5.00% | 5.00% |
| Surfactant (SLS) | 0.50% | — | — | — | — | — | — | 0.49% | 0.49% | 0.49% |
| Surfactant (ALE3S) | — | — | — | — | — | — | 0.49% | — | — | — |
| Polysorbate 20 | — | — | — | — | — | — | — | — | 1.00% | 1.00% |
| salt | — | — | — | — | — | — | 0.02% | — | — | — |
| Citric acid | 0.02% | — | — | — | — | — | 0.02% | 0.02% | 0.02% | 0.02% |
| preservative | 1.45% | 1.45% | 1.45% | 1.45% | 1.45% | 1.45% | 1.45% | 1.45% | 2.2% | 0.05% |
| perfume | 0.20% | 0.20% | 0.20% | 0.20% | 0.20% | 0.20% | 0.20% | 0.50% | — | — |
| AMP | 0.08% | 0-0.1% | — | 0-0.1% | 0-0.1% | 0-0.1% | 0.08% | 0-0.1% | — | — |
| water | QS to 100 | QS to 100 | QS to 100 | QS to 100 | QS to 100 | QS to 100 | QS to 100 | QS to 100 | QS to 100 | QS to 100 |

The preferred Dimethicone (DMF/PDMS) used in the Examples shown in Tables IV to VI is sold by Shin-Etsu Silicones under the tradenames DMF and TMF fluid, Dimethyl Silicone Fluid KF96A and KM96H series; the preferred dimethicone copolyol is sold by Shin-Etsu Silicones under the tradename KF6000 series and the preferred Acrylates/Vinyl Isodecanoate Crosspolymer used is sold by 3V Sigma SPA under the tradename Stabylene 30.

The Examples were prepared as follows: The non-volatile silicone fluid, the silicone surfactants and any further surfactant is premixed and added to the water under continuous stirring. All other ingredients are added to the mixture and the mixture is stirred until a homogeneous emulsion is achieved, but at least for another 1 hour.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of providing shine to hair comprising:
   a. providing an ethanol free, silicone in water emulsion comprising:
      i. from about 0.1% to about 10%, by weight of the emulsion, of a non-volatile polysiloxane fluid;
      ii. from about 0.003% to about 0.6%, by weight of the emulsion, of a rheology modifier;
   b. applying the emulsion on to a hair fibres;
      wherein the emulsion is applied as a spray and the spray comprises droplets with a particle size from about 0.01 µm to about 10 µm;
      wherein the emulsion is applied to more than 25% of hair fibres;
   c. leaving the emulsion on the hair fibres to dry without rinsing to form a film of non-volatile polysiloxane on the hair fibres; wherein the film comprises a film thickness of from about 100 nm to about 500 nm.

2. The method according to claim 1, wherein the emulsion comprises a viscosity of less than 2 Pa*s.

3. The method according to claim 1, wherein the particle size of the spray is from about 0.1 µm to about 1 µm.

4. The method according to claim 1, wherein the particle size of the spray is from about 0.3 µm to about 0.8 µm.

5. The method according to claim 1, wherein the film thickness is from about 100 nm to about 300 nm.

6. The method according to claim 1, wherein less than 0.01 g of the non-volatile polysiloxane per gram of hair is applied.

7. The method according to claim 1, wherein less than 0.015 g of the non-volatile polysiloxane per gram of hair is applied.

8. The method according to claim 1, wherein the emulsion comprises from about 2.5% to about 7.0%, by weight of the emulsion, of the non-volatile polysiloxane fluid.

9. The method according to claim 1, wherein the emulsion comprises from about 4.0% to about 6.0%, by weight of the emulsion, of the non-volatile polysiloxane fluid.

10. The method according to claim 1, wherein the non-volatile polysiloxane fluid is selected from the group consisting of linear polysiloxane fluids, cyclic polysiloxane fluids, polydimethylsiloxane, dimethiconol, dimethiconol derivates, or mixtures thereof.

11. The method according to claim 1, wherein the emulsion comprises from about 0.05% to about 0.3%, by weight of the emulsion, of the rheology modifier.

12. The method according to claim 1, wherein the rheology modifier is acrylic acid/vinylester copolymer.

13. The method according to claim 1, wherein the composition is applied to more than 35% of the hair fibers and wherein less than 5% of hair fibers are bridged.

14. The method according to claim 1, wherein the contact angle on wet hair is less than 85°.

15. The method according to claim 1 wherein the emulsion further comprises from about 92.0% to about 95.0%, by weight of the emulsion, water.

16. The method according to claim 1 wherein the emulsion comprises a viscosity of less than 7 Pa*s.

17. The method according to claim 1, wherein the emulsion further comprises from about 0.02% to about 2.0%, by weight of the emulsion, of a shining surfactant.

18. The method of claim 17, wherein the shining surfactant is polydimethylsiloxane copolyol.

19. The method according to claim 17, wherein a ratio of nonvolatile polysiloxane fluid to shining surfactant is in the range of from about 88% to about 92% polysiloxane fluid to from about 12% to about 8% shining surfactant.

20. The method according to claim 19, wherein the ratio of polysiloxane fluid to shining surfactant is about 90% polysiloxane to about 10% shining surfactant.

* * * * *